United States Patent
Banet et al.

(10) Patent No.: US 7,004,907 B2
(45) Date of Patent: Feb. 28, 2006

(54) BLOOD-PRESSURE MONITORING DEVICE FEATURING A CALIBRATION-BASED ANALYSIS

(75) Inventors: Matthew J. Banet, Del Mar, CA (US); Henk Visser, San Diego, CA (US)

(73) Assignee: Triage Wireless, Inc., San Diego, CA (US)

( * ) Notice: Subject to any disclaimer, the term of this patent is extended or adjusted under 35 U.S.C. 154(b) by 0 days.

(21) Appl. No.: 10/967,610

(22) Filed: Oct. 18, 2004

(65) Prior Publication Data

US 2005/0228301 A1    Oct. 13, 2005

Related U.S. Application Data

(63) Continuation-in-part of application No. 10/709,014, filed on Apr. 7, 2004.

(51) Int. Cl.
*A61B 5/02*    (2006.01)

(52) U.S. Cl. ..................... 600/485; 600/504
(58) Field of Classification Search ............. 600/300, 600/301, 485–507
See application file for complete search history.

(56) References Cited

U.S. PATENT DOCUMENTS

| | | | |
|---|---|---|---|
| 4,320,767 A | 3/1982 | Villa-Real | |
| 4,869,261 A | 9/1989 | Penaz | |
| 5,140,990 A | 8/1992 | Jones et al. | |
| 5,309,916 A * | 5/1994 | Hatschek | 600/485 |
| 5,368,039 A | 11/1994 | Moses | |
| 5,551,438 A | 9/1996 | Moses | |
| 6,050,940 A | 4/2000 | Braun et al. | |
| 6,176,831 B1 | 1/2001 | Voss et al. | |
| 6,336,900 B1 | 1/2002 | Alleckson et al. | |
| 6,364,842 B1 | 4/2002 | Amano et al. | |
| 6,375,614 B1 | 4/2002 | Braun et al. | |
| 6,398,727 B1 | 6/2002 | Bui et al. | |
| 6,413,223 B1 | 7/2002 | Yang et al. | |
| 6,443,906 B1 * | 9/2002 | Ting et al. | 600/490 |
| 6,475,146 B1 * | 11/2002 | Frelburger et al. | 600/437 |
| 6,475,153 B1 | 11/2002 | Khair et al. | |
| 6,514,211 B1 | 2/2003 | Baura | |
| 6,533,729 B1 * | 3/2003 | Khair et al. | 600/503 |
| 6,546,269 B1 | 4/2003 | Kurnik | |
| 6,605,038 B1 | 8/2003 | Teller et al. | |
| 6,609,023 B1 | 8/2003 | Fischell et al. | |
| 6,612,984 B1 | 9/2003 | Kerr, II | |
| 6,616,613 B1 * | 9/2003 | Goodman | 600/504 |
| 6,740,045 B1 * | 5/2004 | Amano | 600/485 |

* cited by examiner

*Primary Examiner*—Robert L. Nasser
*Assistant Examiner*—Patricia C. Mallari

(57)     ABSTRACT

A monitoring device (10), method and system are disclosed herein. The monitoring device (10) utilizes a vital sign monitor (16) to determine a plurality of vital signs of the user. The vital sign monitor (16) preferably comprises a light source (3) and photodetector (31) in communication with a pulse oximetry circuit (35).

11 Claims, 9 Drawing Sheets

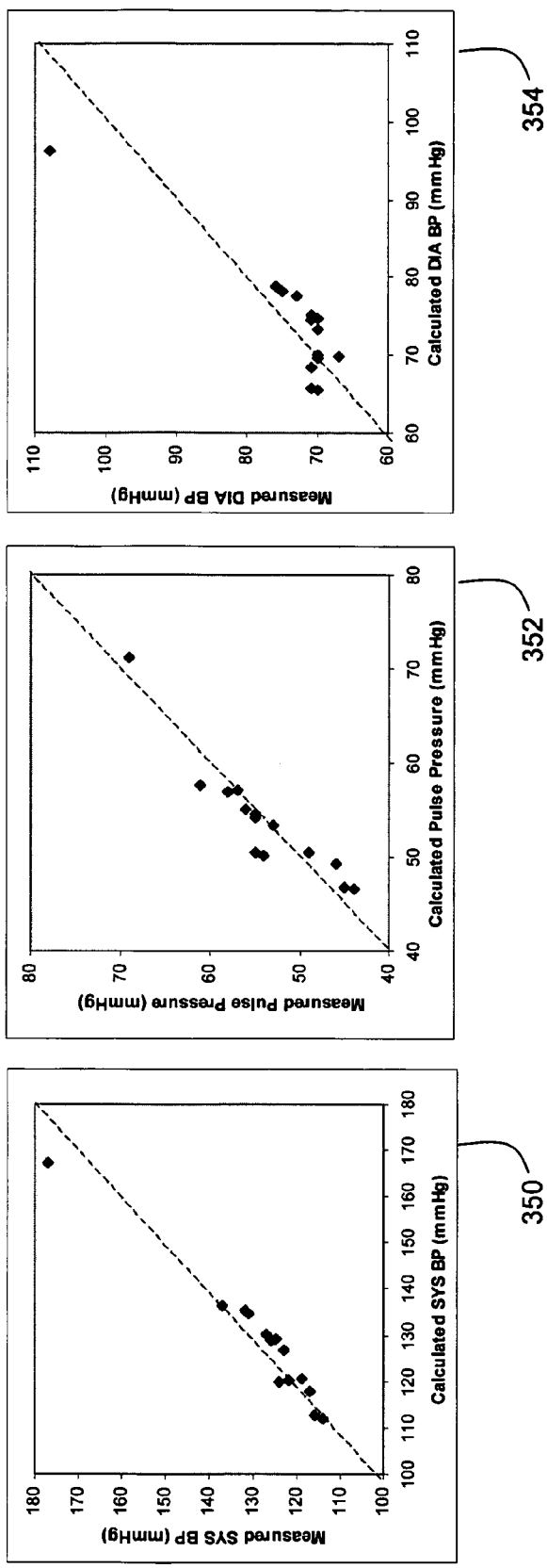

BLOOD-PRESSURE MONITORING DEVICE FEATURING A CALIBRATION-BASED ANALYSIS

CROSS REFERENCES TO RELATED APPLICATION

This application is a continuation-in-part application of U.S. patent application Ser. No. 10/709,014, filed on Apr. 7, 2004.

STATEMENT REGARDING FEDERALLY SPONSORED RESEARCH OR DEVELOPMENT

Not Applicable

BACKGROUND OF THE INVENTION

1. Field of the Invention

The present invention relates to devices for monitoring a patient's vital signs. More specifically, the present invention relates to devices for monitoring blood pressure.

2. Description of the Related Art

Blood within a patient's body is characterized by a baseline pressure value, called the diastolic pressure. Diastolic pressure indicates a pressure in an artery when the blood it contains is static. A heartbeat forces a time-dependent volume of blood through the artery, causing the baseline pressure to increase in a pulse-like manner to a value called the systolic pressure. The systolic pressure indicates a maximum pressure in a portion of the artery that contains a flowing volume of blood.

Pressure in the artery periodically increases from the diastolic pressure to the systolic pressure in a pulsatile manner, with each pulse corresponding to a single heartbeat. Blood pressure then returns to the diastolic pressure when the flowing pulse of blood passes through the artery.

Both invasive and non-invasive devices can measure a patient's systolic and diastolic blood pressure. A non-invasive medical device called a sphygmomanometer measures a patient's blood pressure using an inflatable cuff and a sensor (e.g., a stethoscope) that detects blood flow by listening for sounds called the Korotkoff sounds. During a measurement, a medical professional typically places the cuff around the patient's arm and inflates it to a pressure that exceeds the systolic blood pressure. The medical professional then incrementally reduces pressure in the cuff while listening for flowing blood with the stethoscope. The pressure value at which blood first begins to flow past the deflating cuff, indicated by a Korotkoff sound, is the systolic pressure. The stethoscope monitors this pressure by detecting strong, periodic acoustic 'beats' or 'taps' indicating that the blood is flowing past the cuff (i.e., the systolic pressure barely exceeds the cuff pressure). The minimum pressure in the cuff that restricts blood flow, as detected by the stethoscope, is the diastolic pressure. The stethoscope monitors this pressure by detecting another Korotkoff sound, in this case a 'leveling off' or disappearance in the acoustic magnitude of the periodic beats, indicating that the cuff no longer restricts blood flow (i.e., the diastolic pressure barely exceeds the cuff pressure).

Low-cost, automated devices measure blood pressure using an inflatable cuff and an automated acoustic or pressure sensor that measures blood flow. These devices typically feature cuffs fitted to measure blood pressure in a patient's wrist, arm or finger. During a measurement, the cuff automatically inflates and then incrementally deflates. A microcontroller in the automated device monitors variations in pressure and processes these values to calculate blood pressure. Cuff-based blood-pressure measurements such as these typically only determine the systolic and diastolic blood pressures; they do not measure dynamic, time-dependent blood pressure.

Time-dependent blood pressure can be measured with a device called a tonometer. The tonometer typically features a sensitive transducer positioned on the patient's skin above an underlying artery. The tonometer compresses the artery against a portion of bone while the transducer measures blood pressure in the form of a time-dependent waveform. The waveform features a baseline that indicates the diastolic pressure, and time-dependent pulses, each corresponding to individual heartbeats. The maximum value of each pulse is the systolic pressure. The rising and falling edges of each pulse correspond to pressure values that lie between the systolic and diastolic pressures.

Data indicating blood pressure are most accurately measured during a patient's appointment with a medical professional, such as a doctor or a nurse. Once measured, the medical professional manually records these data in either a written or electronic file. Appointments typically take place a few times each year. Unfortunately, in some cases, patients experience 'white coat syndrome' where anxiety during the appointment affects the blood pressure that is measured. White coat syndrome typically elevates a patient's heart rate and blood pressure; this, in turn, can lead to an inaccurate diagnoses.

Some medical devices for measuring blood pressure and other vital signs include systems for transmitting data from a remote site, such as the patient's home, to a central database. These systems can include a conventional computer modem that transmits data through a telephone line to the database. Or alternatively they can include a wireless transmitter, such as a cellular telephone, which wirelessly transmits the data through a wireless network.

Pulse oximeters are devices that measure variations in a patient's arterial blood volume. These devices typically feature a light source that transmits optical radiation through the patient's finger to a photodetector. A processor in the pulse oximeter monitors time and wavelength-dependent variations in the transmitted radiation to determine heart rate and the degree of oxygen saturation in the patient's blood. Various methods have been disclosed for using pulse oximeters to obtain arterial blood pressure values for a patient. One such method is disclosed in U.S. Pat. No. 5,140,990 to Jones et al., for a 'Method Of Measuring Blood Pressure With a Photoplethysmograph'. The '990 Patent discloses using a pulse oximeter with a calibrated auxiliary blood pressure to generate a constant that is specific to a patient's blood pressure. Another method for using a pulse oximeter to measure blood pressure is disclosed in U.S. Pat. No. 6,616,613 to Goodman for a 'Physiological Signal Monitoring System'. The '613 Patent discloses processing a pulse oximetry signal in combination with information from a calibrating device to determine a patient's blood pressure.

BRIEF SUMMARY OF THE INVENTION

The present invention measures a patient's blood pressure using a cuffless device. The cuffless device wirelessly sends the information to an Internet-accessible website. With the present invention accurate measurements can be made in an ambulatory manner at a patient's home, office or elsewhere outside of a conventional medical facility.

One aspect of the present invention is a device for monitoring a patient's blood pressure that includes: 1) a vital-sign monitor featuring an optical module for monitoring a flow of blood through an artery of the patient; 2) a microprocessor configured to receive a signal from the vital-sign monitor and compare it to a mathematical model to generate a blood-pressure value for the patient; and 3) a short-range wireless transceiver that transmits the blood-pressure value from the device.

Another aspect of the present invention is a method for monitoring a patient's blood pressure that includes the following steps: 1) obtaining at least one numerical calibration curve describing the patient's blood pressure; 2) generating an optical waveform based on the flow of blood through the patient's artery; 3) fitting the optical waveform to determine calibration parameters describing a blood-pressure value; 4) comparing the calibration parameters to the at least one numerical calibration curve to determine the blood-pressure value; and 5) wirelessly transmitting the blood-pressure value.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 9 is an image of three different graphs comparing blood pressure measured with a conventional cuff (y-axis) to blood pressure measured using the monitoring system of FIG. 1 (x-axis).

DETAILED DESCRIPTION OF THE INVENTION

Figure 1:
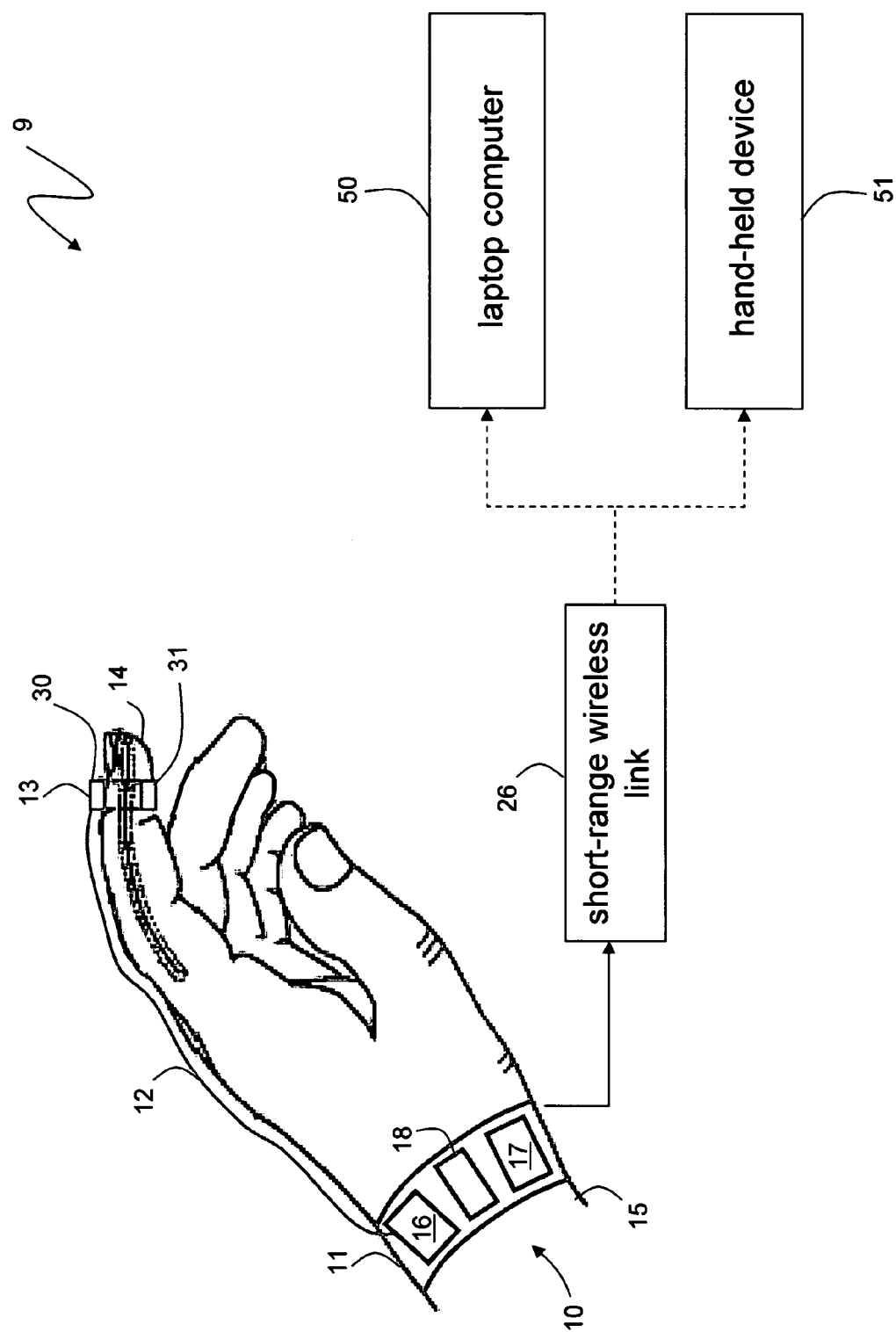
FIG. 1 is a schematic side view of a monitoring system for measuring vital signs according to the present invention.
Figure 2:
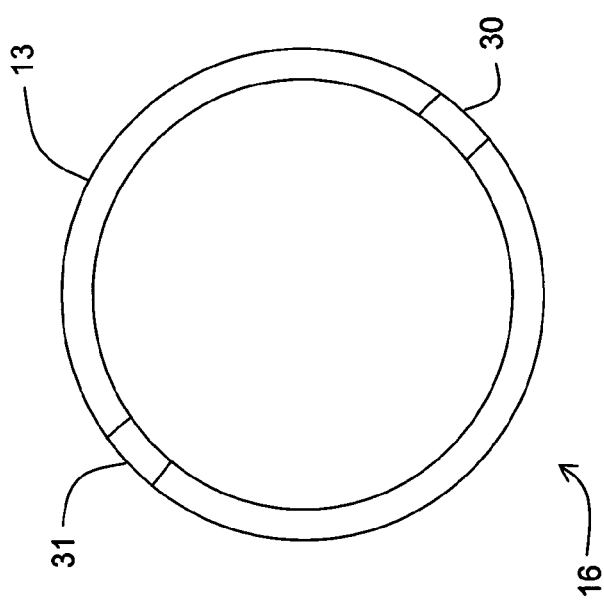
FIG. 2 is an isolated cross-sectional view of a finger-mounted module used in the monitoring system of FIG. 1.
Figure 3:
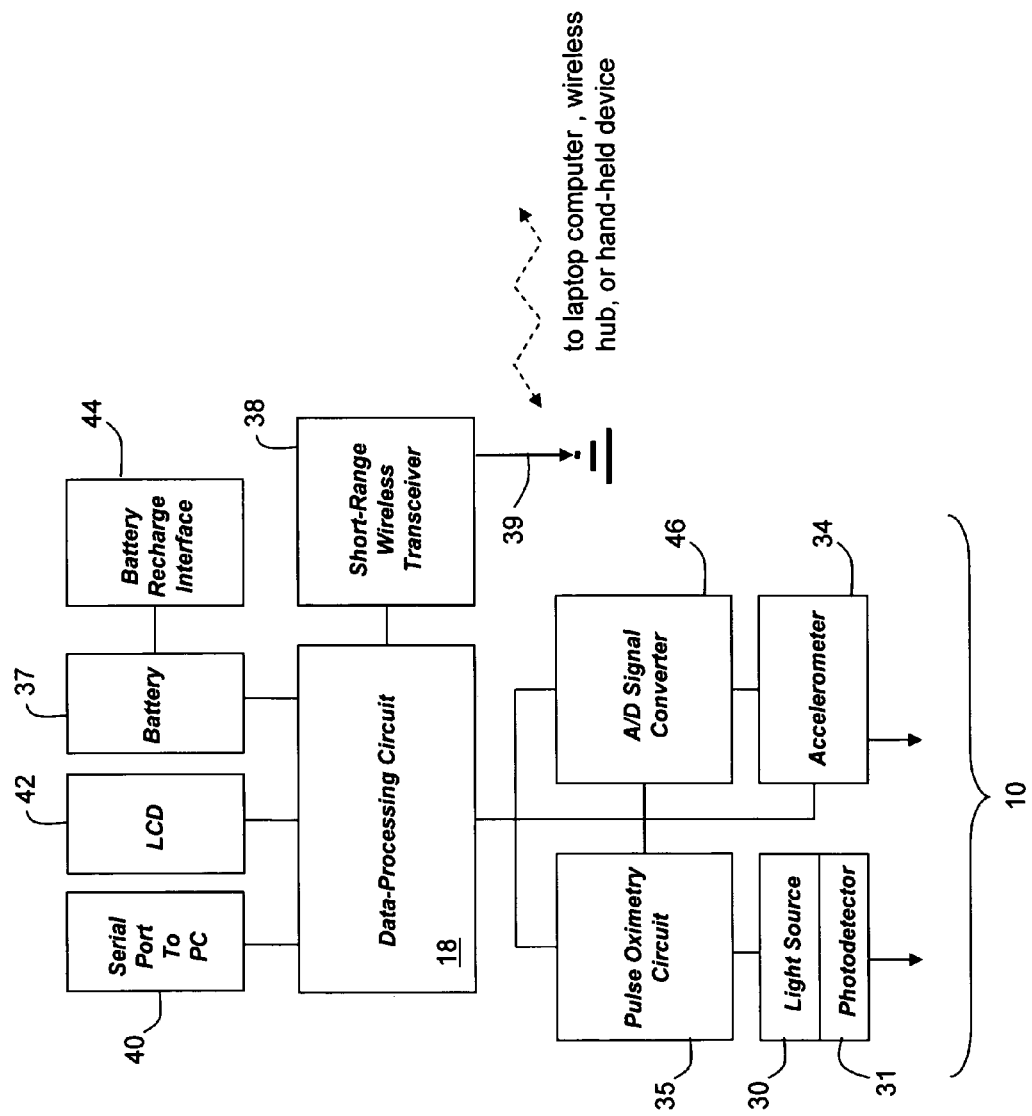
FIG. 3 is a schematic view of circuit components used in the monitoring system of FIG. 1.

FIGS. 1–3 show a monitoring system 9 that measures the vital signs of a user. The system 9 features a monitoring device 10 that measures and wirelessly transmits the measurements through a short-range wireless link 26 to an external laptop computer 50 or hand-held device 51 for further processing with a software program stored in a memory, or for transmission over a network such as disclosed in co-pending U.S. patent application Ser. No. 10/810,237, filed Mar. 26, 2004, for a CUFFLESS BLOOD PRESSURE MONITOR AND ACCOMPANYING WEB SERVICES INTERFACE; co-pending U.S. patent application Ser. No. 10/709,015, filed Apr. 7, 2004, for a CUFF-LESS BLOOD-PRESSURE MONITOR AND ACCOMPANYING WIRELESS, INTERNET-BASED SYSTEM; or co-pending U.S. patent application Ser. No. 10/752,198, filed Jan. 6, 2004, for a WIRELESS, INTERNET-BASED MEDICAL DIAGNOSTIC SYSTEM, all of which are hereby incorporated by reference in their entirety. The monitoring device 10 preferably includes a wrist-mounted module 11 that attaches to an area of the user's wrist 15 where a watch is typically worn, and a finger-mounted module 13 that attaches to the user's index finger 14. A cable 12 preferably provides an electrical connection between the finger-mounted module 13 and wrist-mounted module 11.

Referring to FIG. 3, in a preferred embodiment, the wrist-mounted module 11 preferably comprises a data-processing circuit 18 that includes a microprocessor, a short-range wireless transceiver 38, a pulse oximetry circuit 35, a battery 37 and an antenna 39. The components are preferably embedded within a comfortable, non-conductive material, such as neoprene rubber, that wraps around the patient's wrist.

The microprocessor within the data-processing circuit 18 directs the monitoring device 10. The term 'microprocessor', as used herein, preferably means a silicon-based microprocessor or microcontroller that operates compiled computer code to perform mathematical operations on data stored in a memory. Examples include ARM7 or ARM9 microprocessors manufactured by a number of different companies; AVR 8-bit RISC microcontrollers manufactured by Atmel; PIC CPUs manufactured by Microchip Technology Inc.; and high-end microprocessors manufactured by Intel and AMD.

The short-range wireless transceiver 38 is preferably a transmitter operating on a wireless protocol, e.g. Bluetooth™, part-15, 802.15.4 or 802.11. "Part-15" refers to a conventional low-power, short-range wireless protocol, such as that used in cordless telephones. The short-range wireless transceiver 38 (e.g., a Bluetooth™ transmitter) receives information from the data-processing circuit 18 and transmits this information in the form of a packet through an antenna 39. The external laptop computer 50 or hand-held device 51 features a similar antenna coupled to a matched wireless, short-range receiver that receives the packet. In certain embodiments, the hand-held device 51 is a cellular telephone with a Bluetooth™ circuit and antenna integrated directly into a chipset used in the cellular telephone. In this case, the cellular telephone may include a software application that receives, processes, and displays the information. The hand-held device 51 may also include a long-range wireless transmitter that transmits information over a terrestrial, satellite, or 802.11-based wireless network. Suitable networks include those operating at least one of the following protocols: CDMA, GSM, GPRS, Mobitex, DataTac, iDEN, and analogs and derivatives thereof.

A vital-sign monitor 16 connects to the finger-mounted module 13 and measures information that is processed to determine the user's vital signs. Specifically, the vital-sign monitor 16 connects to a light source 30 and photodetector 31 embedded in the finger-mounted module 13 that measure blood flow in the user's finger, and sends this information through the cable 12 to the wrist-mounted module 11. The finger-mounted module 13 is preferably composed of a flexible polymer material. The light source 30 typically includes light-emitting diodes that generate both red ($\lambda$~630 nm) and infrared (λ~900 nm) radiation. As the heart pumps blood through the patient's finger, blood cells absorb and transmit varying amounts of the red and infrared radiation depending on how much oxygen binds to the cells' hemoglobin. The photodetector 31 detects transmission at the red and infrared wavelengths, and in response generates a radiation-induced current that travels through the cable 12 to the pulse-oximetry circuit 35 embedded within the wrist-mounted module 11. The pulse-oximetry circuit 35 connects to an analog-to-digital signal converter 46. The analog-to-digital signal converter 46 converts the radiation-induced current into a time-dependent optical waveform, which is then sent back to the pulse-oximetry circuit 35 and analyzed to determine the user's vital signs as described in this application and the above-mentioned co-pending patent applications, the contents of which have been incorporated by reference.

Additional software programs can further analyze blood pressure, and heart rate, and pulse oximetry values to characterize the user's cardiac condition. These programs, for example, may provide a report that features statistical analysis of these data to determine averages, data displayed in a graphical format, trends, and comparisons to doctor-recommended values.

FIG. 3 shows, in detail, electronic components featured in the monitoring device 10. In a preferred embodiment, the pulse-oximetry circuit 35 connects to the analog-to-digital converter 46 within the data-processing circuit 18. A battery 37 powers all the electrical components within the monitoring device 10, and is typically a metal hydride battery (generating 5–7V) that can be recharged through a battery recharge interface 44. The monitoring device 10 can include an LCD 42 that displays information for the user or patient. In another embodiment, the data-processing circuit 18 avails calculated information through a serial port 40 to an external personal computer, which then displays and analyzes the information using a client-side software application. In yet another alternate embodiment, the monitoring device 10 includes an accelerometer 34 or alternative motion-detecting device to determine when the patient' hand is at rest, thereby reducing motion-related artifacts introduced to the measurement.

Figure 4:
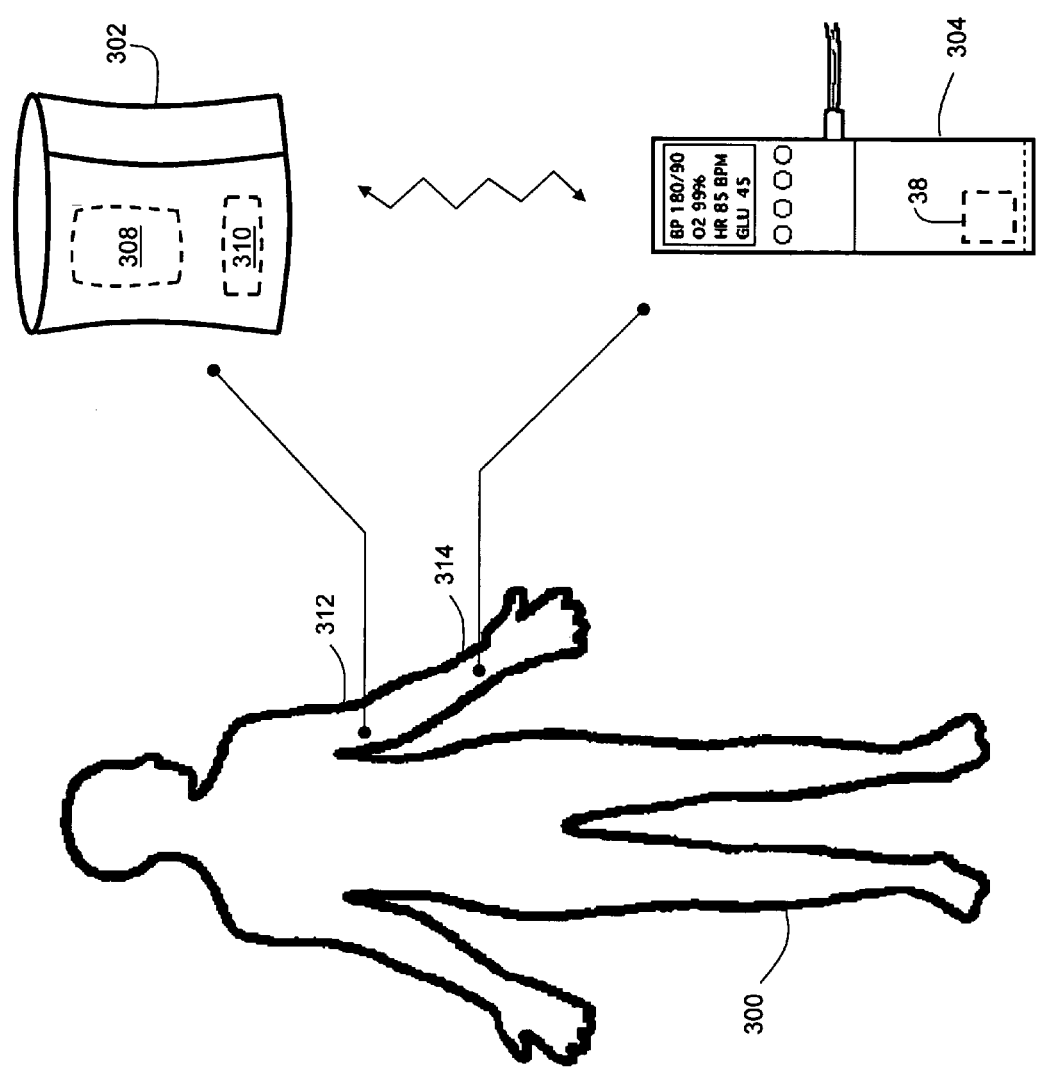
FIG. 4 is a schematic diagram of a calibration system used with the monitoring system of FIG. 1 to determine blood pressure.

FIG. 4 shows schematically how the above-described monitoring device 10 measures blood pressure from a patient 300 using a calibration-based approach. In a preferred embodiment, the monitoring device 10 measures blood pressure using calibration parameters in combination with an optical measurement made using the monitoring device 10 described in FIGS. 1–3. Calibration parameters are determined prior to a measurement using a calibration device 302, typically a conventional blood-pressure cuff, that temporarily attaches to an upper portion 312 of the patient's arm. Immediately prior to measuring the calibration parameters, a short-range radio transmitter 310 embedded in the calibration device 302 sends a wireless signal to the short-range wireless transceiver 38 in the monitoring device 10 worn on the patient's wrist 314. The signal indicates that the calibration measurement is about to begin. Once the signal is received, the calibration device 302 and monitoring device 10 simultaneously collect, respectively, blood pressure values (systolic, diastolic pressures) and a corresponding optical waveform. The calibration device 302 measures systolic and diastolic blood pressure using a cuff coupled to a motor-controlled pump and data-processing electronics. The short-range radio transmitter sends systolic and diastolic blood pressure values wirelessly to the monitoring device 10 once the calibration measurement is completed. This process is repeated at a later time (e.g., 15 minutes later) to collect a second set of calibration parameters. The calibration device 302 is then removed.

Figure 5:
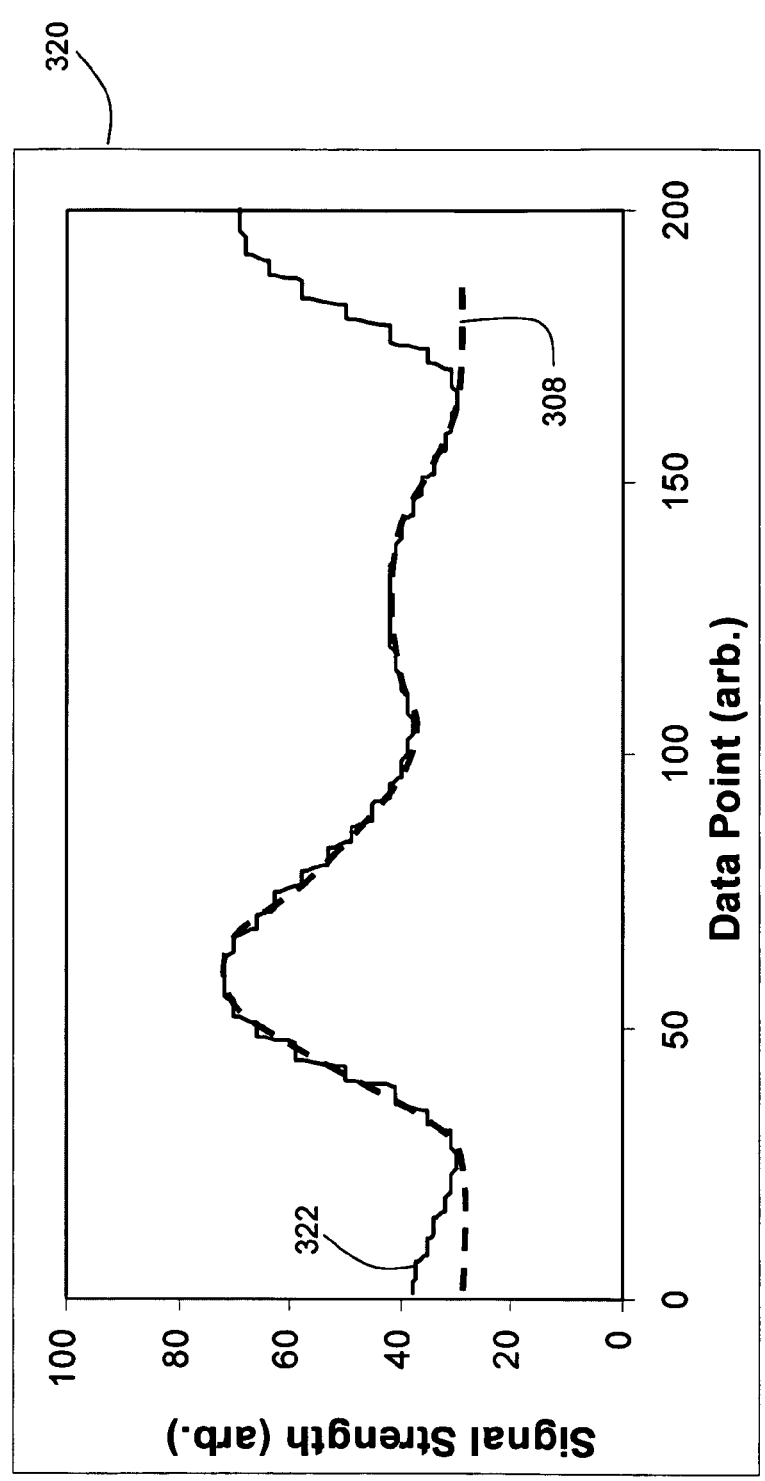
FIG. 5 is a graph of a single pulse from an optical waveform and a corresponding mathematical 'fit' generated with the monitoring system of FIG. 1.

The systolic and diastolic blood pressure values measured with the calibration device 302, along with their corresponding optical waveforms, are stored in memory in the monitoring device 10 and then analyzed with the data-processing circuit 18 as described in detail below to complete the calibration. FIG. 5 features a graph 320 that indicates how this analysis is performed on a single pulse 322 from the optical waveform. Once collected, the pulse 322 is 'fit' using a mathematical function that accurately describes the pulse's features, and an algorithm (e.g., the Marquardt-Levenberg algorithm) that iteratively varies the parameters of the function until it best matches the time-dependent features of the pulse 322. The graph 320 includes a dashed line showing a mathematical function 308 that represents the fit. The mathematical function 308 is composed of numerical parameters can be easily stored in memory and analyzed with the data-processing circuit 18 to calibrate the monitoring device 10.

Figure 6:
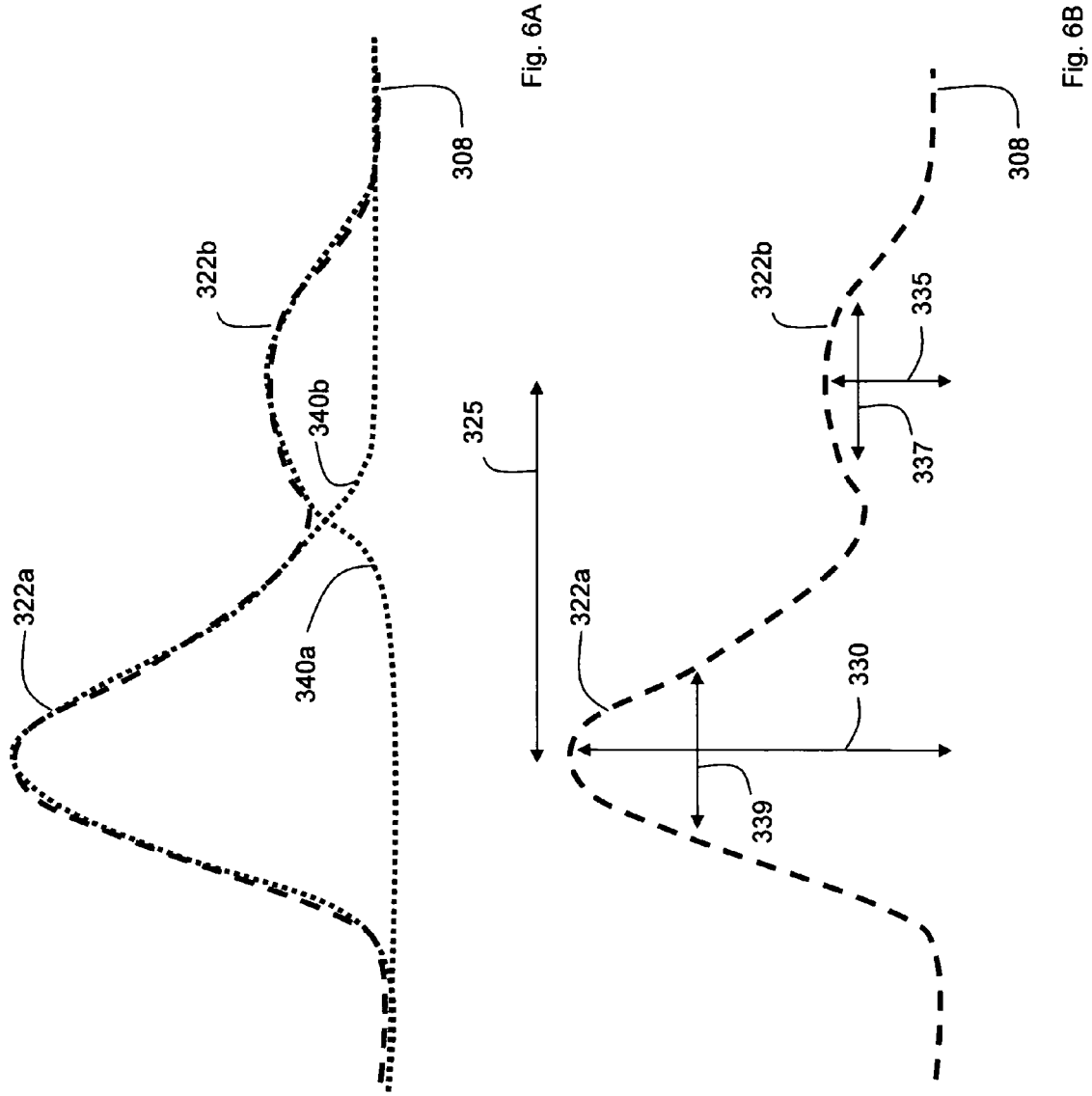
FIG. 6A is a graph of the mathematical fit of FIG. 5 along with mathematical components used to represent a mathematical model according to the invention.
FIG. 6B is a graph of the mathematical fit of FIG. 5.

FIGS. 6A and 6B show how the data-processing circuit can analyze the mathematical function 308 of FIG. 5 to yield calibration parameters required for the blood-pressure measurement according to the invention. As shown in FIG. 6A, the mathematical function 308 comes from a mathematical model that describes blood dynamics in the patient's body. The mathematical model accounts for primary and reflected 'waves' within the optical waveform. The primary wave, shown as the first peak 322a in the mathematical function 308, results from a pressure wave traveling through the patient's arteries following systole. The pressure wave causes a short, time-dependent increase in volume of blood as measured in an artery in the patient's extremities (e.g., a finger) by the light source and photodetector. Some energy from the primary wave reflects back to the extremities from various sites in the patient's vascular tree, causing the reflected wave. This increases the blood volume in the patient's extremities at a slightly later time as measured by the light source and photodetector, resulting in a second peak 322b in the mathematical function 308.

Separate components 340a, 340b within the mathematical model represent, respectively, the primary and reflected waves, and can thus be used to model the first 322a and second 322b peaks in the mathematical function 308. In a simple model, as shown in FIG. 6A, both components 340a, 340b can be represented by Gaussian functions $f_{p,r}(t)$:

$$f_{p,r}(t) = \frac{A_{p,r}}{\sigma_{p,r}\sqrt{2\pi}} \exp-((x-u_{p,r})^2/2\sigma_{p,r}^2)$$

where $A_{p,r}$ represents the amplitude of either the primary (p) or reflected (r) wave, $\sigma_{p,r}$ represents the width of these waves, and $u_{p,r}$ represents a point in time at which the wave's peak amplitude is reached. The second component 340b has a relatively small amplitude $(A_r)$ and large width $(\sigma_r)$ because the reflected wave disperses (causing it to widen) and attenuates due to reflection (causing its amplitude to lessen) as it propagates through the patient's circulatory system. FIG. 6B shows how $A_{p,r}$, $\sigma_{p,r}$, and $u_{p,r}$ relate to the mathematical function 308. The amplitude and central position of the primary wave, indicated by the arrow 330, represent $A_p$ and $u_p$, respectively. Similarly, the amplitude and central position of the reflected wave, indicated by the arrow 335, represent $A_r$ and $u_r$, respectively. The widths of primary and reflected waves, indicated respectively by arrows 339 and 337, represent $\sigma_p$ and $\sigma_r$. Arrow 325 represents the difference in the central positions of the primary and reflected wave, i.e. $u_p$–$u_r$.

Combinations of the calibration parameters may also be used in the blood-pressure measurement. For example, a ratio between the reflected and primary waves' maximum amplitudes ($A_r/A_p$) may be used as a calibration parameter. In addition, an optical waveform may be numerically processed before it is fit with the mathematical model as a way of maximizing the effectiveness of the fit and consequently the accuracy of the blood-pressure measurement. For example, the data-processing circuit 18 may run an algorithm that takes a second derivative of the waveform as a way of isolating the first and second peaks. This is especially useful if these peaks are merged together within the waveform. In addition, in an effort to improve the signal-to-noise ratio of the optical waveform, the data-processing circuit may average multiple waveforms together. Alternatively, the data processing circuit 18 reduces high-frequency noise within the optical waveform using a relatively simple multiple-point smoothing algorithm, or a relatively complicated algorithm based on Fourier analysis.

Figure 7:
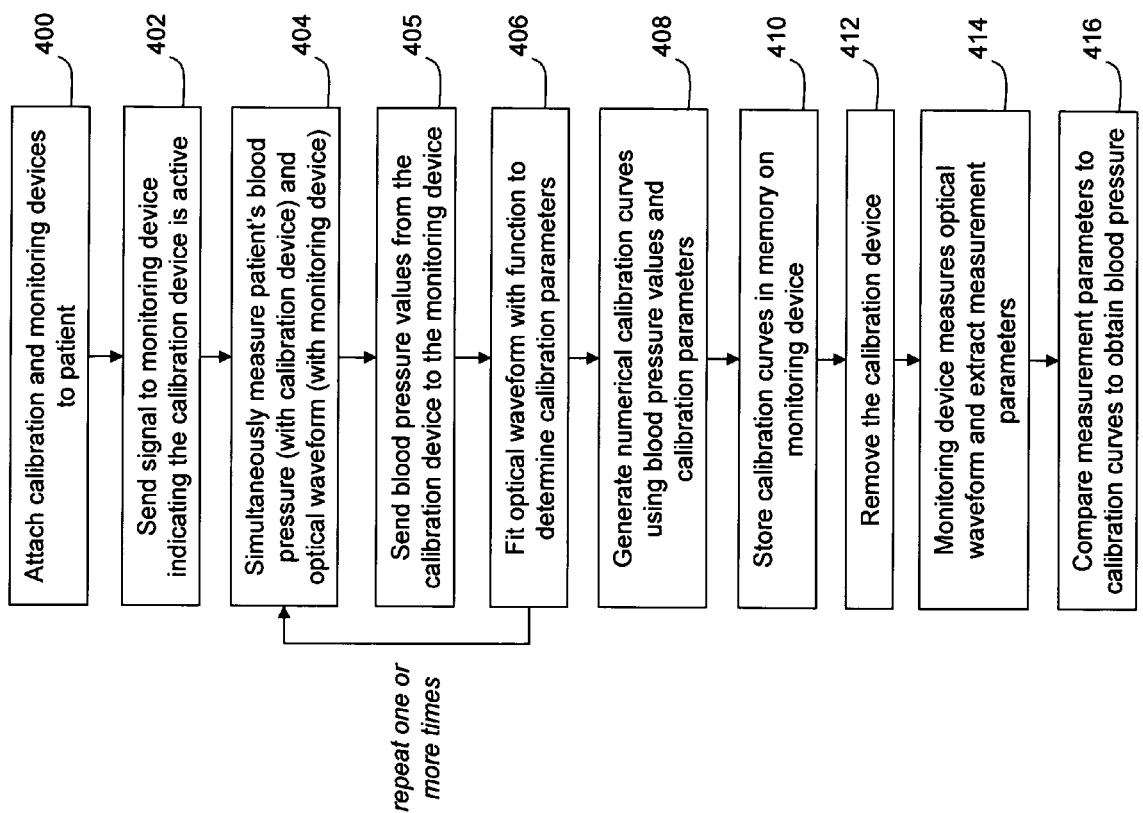
FIG. 7 is a flow chart of the calibration process used with the monitoring system of FIG. 1 and the calibration system of FIG. 4.

FIG. 7 illustrates a flow chart of a preferred method of utilizing the calibration parameters $A_{p,r}$, $\sigma_{p,r}$, and $u_{p,r}$ are measured and processed to perform a blood-pressure measurement according to the present invention. As shown in the figure, the arm-worn calibration device 302 is attached to the patient (box 400) at block 402, the calibration device 302 sends a signal preferably via Bluetooth™ to the wrist-mounted monitoring device 304 to indicate that the calibration device is active. At block 404, the calibration device 302 then makes a conventional cuff-based blood-pressure measurement while the monitoring device 304 simultaneously measures an optical waveform from the patient. At block 405, the calibration device then sends the blood-pressure values via Bluetooth™ to the monitoring device 304. At block 406, a mathematical model operating on the data-processing circuit 18 of the monitoring device 304 fits the optical waveform to extract $A_{p,r}$, $\sigma_{p,r}$, and $u_{p,r}$, which are used as calibration parameters. This process is preferably repeated at least one more time at a later time to extract $A_{p,r}$, $\sigma_{p,r}$, and $u_{p,r}$ corresponding to a second blood-pressure value. At block 408, this information is then processed to generate numerical calibration curves that correlate the calibration parameters to actual blood-pressure values. At block 410, the monitoring device 304 stores the calibration curves in its memory (box 410) for use in subsequent measurements. At block 412, the patient then removes the calibration device 304, at block 414 the monitoring device 304 performs continuous measurements, typically over a period lasting 24–48 hours, to determine $A_{p,r}$, $\sigma_{p,r}$, and $u_{p,r}$ (box 414). The values for $A_{p,r}$, $\sigma_{p,r}$, and $u_{p,r}$ obtained during the continuous measurements are then compared to the stored calibration curves to determine the patient's blood pressure.

Figure 8:
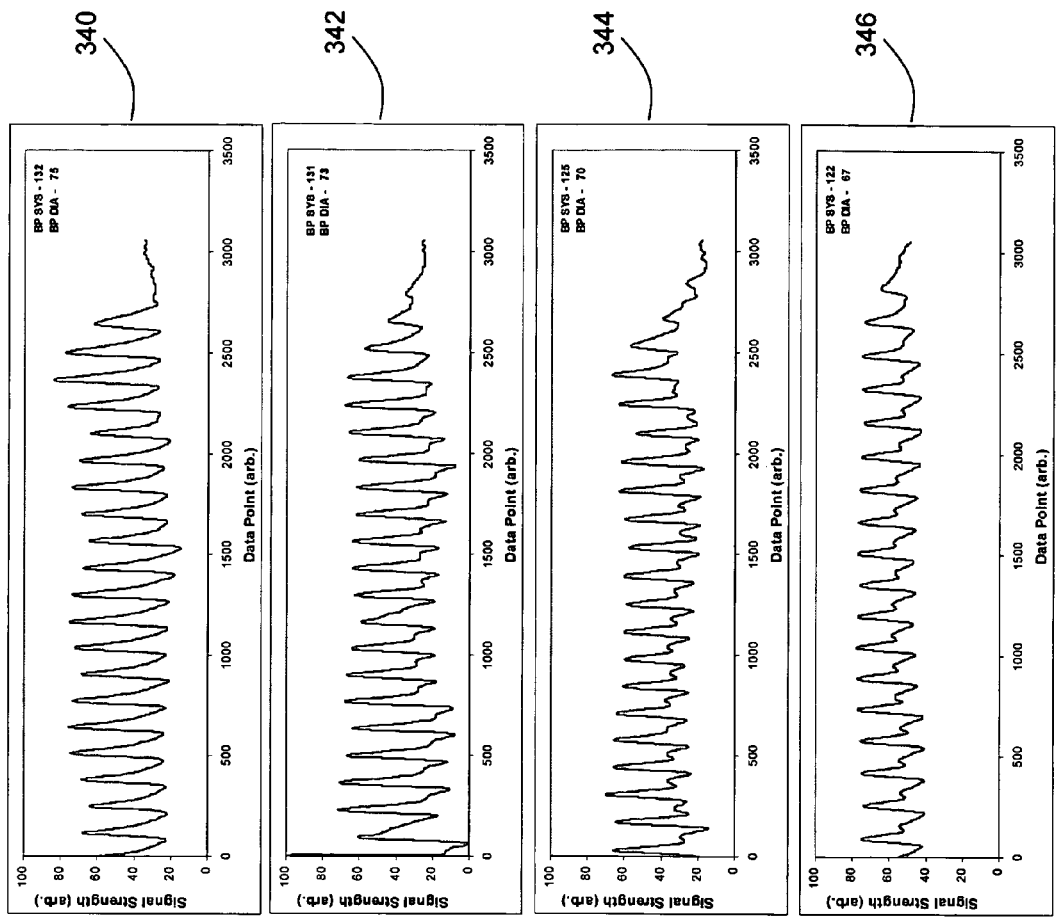
FIG. 8 is an image of four different graphs of optical waveforms for four different blood pressure measurements made with the monitoring system of FIG. 1.

FIG. 8 shows how pulses within the optical waveform vary with blood pressure, and can therefore be processed as described above. The figure includes four optical waveforms 340, 342, 344, 346, each corresponding to a different blood pressure. The first optical waveform 340 corresponds to a blood pressure of 132 mmHg (systolic) and 75 mmHg (diastolic) and features a heart rate of 110 bpm; the reflected wave is absent, and thus the ratio between the reflected and primary waves is 0. In the second waveform 342, the heart rate decreases to 106 bpm, and blood pressure correspondingly decreases to 131 mmHg (systolic) and 73 mmHg (diastolic). The reflected wave begins to appear in the second waveform 342, resulting in a ratio between the reflected and primary peaks of 0.19. The third 344 and fourth 346 waveforms show that the patient's heart rate decreases and the ratio increases as both systolic and diastolic blood pressure continue to decrease. Table 1, below, describes these relationships in more detail.

TABLE 1 relationship between blood pressure and calibration parameters

| Optical Waveform | Heart Rate (bpm) | Ratio of Secondary/Primary Waves | Systolic BP (mmHg) | Diastolic BP (mmHg) |
|---|---|---|---|---|
| 340 | 110 bpm | 0.0 | 132 | 76 |
| 342 | 106 bpm | 0.19 | 131 | 73 |
| 344 | 103 bpm | 0.30 | 126 | 70 |
| 346 | 89 bpm | 0.34 | 122 | 67 |

FIG. 9 indicates the efficacy of the above-described calibration-based approach to measuring blood pressure. The figure includes three graphs 350, 352, 354 that compare blood pressure measured with a conventional cuff (y axis) to blood pressure calculated using a calibration-based approach following a cuffless measurement (x axis). Each graph 350, 352, 354 includes a dashed line indicating perfect, 1:1 correlation. The first graph 350 shows results for systolic blood pressure. Correlation for these measurements is very good, with the average difference between the conventional and cuffless measurements being 3.2 mmHg. The second graph 352 is for pulse blood pressure (the difference between systolic and diastolic blood pressure) and features an average difference between the conventional and cuffless measurements of 1.9 mmHg. Graph 354 is for diastolic blood pressure and features an average difference between the conventional and cuffless measurements of 3.8 mmHg.

In other embodiments, placement of the optical, mechanical, and electrical modules described above can be modified to change the form factor of the monitoring device 10. Other configurations of the above-described optical, mechanical, and electrical sensors are also within the scope of the invention. The data-processing circuit 18 can also use algorithms other than those described above to process data measured by the wrist 11 and finger-mounted 13 modules. These algorithms are typically based on the equations described above, but may vary in their form. In other embodiments, electrical components within the monitoring device 10 (as shown in FIG. 3) differ from those described above, or are consolidated into a single silicon-based device, such as a custom-made ASIC.

In still other embodiments mathematical functions other than the Gaussian function (e.g., an exponential function), or different methods of analysis, can be used to model both the primary and reflected waves. For example, the data-processing circuit may take a Fourier or Laplace transform of the time-dependent optical waveform to generate a frequency-dependent waveform. The frequency-dependent waveform may then be fit with a mathematical function to analyze the primary and secondary waves. In other methods of analysis, the data-processing circuit may take a first or second derivative of the optical waveform, and the first or second derivative is then analyzed as described above.

The monitoring device 10 is small, easily worn by the user for general day-to-day activities. It makes non-invasive measurements in a matter of seconds with no affect on the user. Furthermore, the on-board microprocessor can analyze the time-dependent measurements to generate detailed statistics (e.g., average values, standard deviations, beat-to-beat pressure variations) that are not available with conventional devices that only measure properties at isolated times.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention:

1. A method for monitoring a patient's blood pressure, the method comprising:
   simultaneously measuring the patient's arterial blood flow with a monitoring device and a calibration blood pressure with a calibration device to obtain at least one numerical calibration curve describing the patient's blood pressure;
   generating an optical waveform based on the flow of blood through an artery of the patient using a vital-sign monitor of the monitoring device, the vital-sign monitor comprising an optical module;
   comparing the optical waveform to a mathematical model that describes a primary wave and a reflected wave in a circulatory system of the patient to determine a plurality of calibration parameters describing a blood-pressure value for the patient;
   comparing the plurality of calibration parameters to the at least one numerical calibration curve to determine a real-time blood-pressure value for the patient; and
   wirelessly transmitting the real-time blood-pressure value for the patient.

2. The method according to claim 1 wherein the plurality of calibration parameters comprises the amplitudes of the primary wave and the reflected wave, the central positions of the primary wave and the reflected wave, and the widths of the primary wave and the reflected wave.

3. The method according to claim 1 further comprising receiving the real-time blood pressure value for the patient at a hand-held device for transmission over a network.

4. The method according to claim 1 wherein the calibration device comprises a cuff coupled to an electronic system.

5. The method according to claim 1 wherein the monitoring device further comprises a pulse oximetry circuit.

6. A method for monitoring a patient's real-time blood pressure, the method comprising:
   simultaneously measuring the patient's arterial blood flow with a monitoring device and a calibration blood pressure with a calibration device to obtain at least one numerical calibration curve describing the patient's blood pressure;
   generating an optical waveform based on the flow of blood through an artery of the patient using the monitoring device, the monitoring device comprising an optical module comprising a light source, a photodetector and a pulse oximetry circuit;
   comparing the optical waveform to a mathematical model that describes a primary wave and a reflected wave in a circulatory system of the patient to determine a plurality of calibration parameters describing a blood-pressure value for the patient;
   comparing the plurality of calibration parameters to the at least one numerical calibration curve to determine a real-time blood-pressure value for the patient; and
   wirelessly transmitting the real-time blood-pressure value for the patient from the monitoring device to a hand-held device.

7. A method for monitoring a patient's blood pressure, the method comprising:
   obtaining at least one numerical calibration curve describing the patient's blood pressure;
   generating an optical waveform based on the flow of blood through the patient's artery;
   fitting the optical waveform to determine calibration parameters describing a blood-pressure value wherein the fitting comprises comparing the optical waveform to a mathematical model that describes a primary wave and a reflected wave in a circulatory system of the patient;
   comparing the calibration parameters to the at least one numerical calibration curve to determine the blood-pressure value; and
   wirelessly transmitting the blood-pressure value.

8. The method according to claim 7 wherein generating the optical waveform comprises sending a signal corresponding to the patient's arterial blood flow to an analog-to-digital converter which converts the signal into the optical waveform.

9. The method according to claim 7 wherein obtaining the at least one numerical calibration curve comprises simultaneously measuring the patient's arterial blood flow with a monitoring device and a calibration blood pressure with a calibration device.

10. The method according to claim 9 wherein obtaining the at least one numerical calibration curve further comprises transmitting the calibration blood pressure from the calibration device to the monitoring device.

11. The method according to claim 10 wherein the calibration blood pressure is wirelessly transmitted from the calibration device using a radio-frequency transceiver operating a wireless protocol based on, part-15, 802.11, or 802.15.4.

* * * * *